(12) United States Patent
Hessler (10) Patent No.: US 11,529,433 B2
(45) Date of Patent: Dec. 20, 2022

(54) BIOTECHNOLOGICALLY-PRODUCED CELLULOSE-CONTAINING ARTICLE FOR DERMATOLOGICAL USE

(71) Applicant: JENACELL GMBH, Jena (DE)

(72) Inventor: Nadine Hessler, Mengersgereuth-Hämmern (DE)

(73) Assignee: JeNaCell GmbH, Jena (DE)

( * ) Notice: Subject to any disclaimer, the term of this patent is extended or adjusted under 35 U.S.C. 154(b) by 360 days.

(21) Appl. No.: 16/914,543

(22) Filed: Jun. 29, 2020

(65) Prior Publication Data

US 2020/0364264 A1 Nov. 19, 2020

Related U.S. Application Data

(62) Division of application No. 15/779,312, filed as application No. PCT/EP2016/072972 on Sep. 27, 2016, now Pat. No. 10,736,823.

(30) Foreign Application Priority Data

Nov. 25, 2015 (EP) .................................. 15196348

(51) Int. Cl.
| | | |
|---|---|---|
| A61K 8/02 | (2006.01) | |
| A61L 2/08 | (2006.01) | |
| A61K 8/73 | (2006.01) | |
| A61Q 19/00 | (2006.01) | |

(52) U.S. Cl.
CPC ............ *A61L 2/087* (2013.01); *A61K 8/0212* (2013.01); *A61K 8/731* (2013.01); *A61Q 19/00* (2013.01); *A61Q 19/007* (2013.01); *A61K 2800/413* (2013.01)

(58) Field of Classification Search
None
See application file for complete search history.

(56) References Cited

U.S. PATENT DOCUMENTS

| | | |
|---|---|---|
| 4,655,758 A | 4/1987 | Ring et al. |
| 2009/0041815 A1 | 2/2009 | Legendre |
| 2009/0054552 A1 | 2/2009 | Yano et al. |
| 2009/0074837 A1 | 3/2009 | Evans et al. |
| 2011/0286948 A1 | 11/2011 | Lin et al. |
| 2013/0004784 A1 | 1/2013 | Hessler et al. |
| 2013/0244977 A1 | 9/2013 | Lee et al. |
| 2015/0225486 A1* | 8/2015 | Hessler ................... C12P 19/04 536/56 |

FOREIGN PATENT DOCUMENTS

| | | |
|---|---|---|
| CN | 101386877 A | 3/2009 |
| CN | 102784071 A | 11/2012 |
| CN | 102791300 A | 11/2012 |
| DE | 10 2004 002 990 A1 | 8/2005 |
| FR | 2 916 971 A1 | 12/2008 |
| JP | 2002004191 A | 1/2002 |
| JP | 200582704 A | 3/2005 |
| JP | 2008061532 A | 3/2008 |
| JP | 2015504845 A | 2/2015 |
| WO | 2007 091801 A1 | 8/2007 |
| WO | 2012 131623 A2 | 10/2012 |
| WO | 2013 094077 A1 | 6/2013 |
| WO | 2016 113400 A1 | 7/2016 |

OTHER PUBLICATIONS

Almeida, I.F., Bacterial cellulose membranes as drug delivery systems: An in vivo skin compatibility study, Eur. J. Pharm. and Biopharm., 2014, pp. 1-5, Elsevier B.V.
Extended European Search Report dated Aug. 30, 2021.
Tamura, Hiroshi, A Polymer, 2006, vol. 55, May issue, p. 344.
Translation of Chinese office action dated Aug. 25, 2020.

* cited by examiner

*Primary Examiner* — Brian Gulledge
(74) *Attorney, Agent, or Firm* — Hudak, Shunk & Farine Co. LPA (57) ABSTRACT

A cellulose-containing article for treating an area of skin, wherein the article comprises BNC in an amount of at least 1% by weight and at most 15% by weight, comprises fluid in an amount of at least 85% by weight and at most 99% by weight, has an average thickness of at least 0.5 mm and at most 8 mm, wherein the BNC is of microbial origin.

23 Claims, 5 Drawing Sheets

BIOTECHNOLOGICALLY-PRODUCED CELLULOSE-CONTAINING ARTICLE FOR DERMATOLOGICAL USE

FIELD OF THE INVENTION

The present invention relates to a biotechnologically produced nano-structured cellulose (BNC)-containing article for treating an area of skin, medical and non-medical methods for the treatment of an area of a subject's skin, and methods of manufacturing said BNC-containing article.

BACKGROUND OF THE INVENTION

It is known in the art that application of pure water provides an excellent possibility to relax and clean skin. However, there is a need to apply a water reservoir, which can interact with the skin and provide moisture to the skin for a prolonged time period and without the need of immersing or bathing the skin. For this purpose cellulose articles are known, which can be applied in order to provide such water reservoir to the skin.

Particularly, bacterial cellulose materials have been used in medical and cosmetic applications in the prior art. This material is an extracellular polysaccharide produced by different bacteria, including *Komatagaibacter*, *Agrobacter* and *Sarcina* strains (I. F. Almeida et al., Bacterial cellulose membranes as drug delivery systems: An in vivo skin compatibility study, Eur. J. Pharm. Biopharm. (2014)).

Methods for producing bacterial-cellulose are known in the art. Particularly, static or discontinuous production processes, like static fermentation, are used. Particularly, bacterial BNC produced by static or discontinuous production processes is known, however, relatively expensive, and comes along with various drawbacks, particularly with disadvantageous or at least sub-optimal properties of the produced bacterial cellulose. Moreover, in static manufacturing processes the production of bacterial BNC is limited by the batch-wise production. The bacterial cellulose produced in such processes is of relatively heavy weight and possesses a disadvantageously low tensile strength. A respective article for application to skin, moreover, needs an additional support or other fixation means. Therefore, such articles usually do not allow a subject moving unimpededly while the article remains on the area of skin. Due to the relatively low tensile strength, the articles of the prior art also easily tear. Moreover, many articles known in the art do not provide a sufficient moisturizing effect without wet feeling and a soft and smooth surface feel at the same time.

In Almeida et al. the authors tested skin compatibility of bacterial cellulose patches by applying the patches to the subject's forearms for 24 hours. The patches contained 5% of water and were fixed to the skin using aluminum chambers. One patch contained 32% of glycerin. The glycerin containing patch showed improved bendability.

The document DE 10 2004 002 990 A1 describes a nano-structured material that can be used as a cosmetic pad or wound dressing. It may be used to achieve a cooling effect by evaporation of liquid contained in the material. However, the nano-structured material is rather thin. If thicker material is used, the material needs a supporting structure for reinforcement. In other embodiments, the material is used together with an adhesive or sewn to the skin. However, this document does not disclose an article capable of adhering to the skin without any fixation means or means to support the article's structural integrity. Additional support or fixation means destroy the soft and smooth surface feel of bacterial cellulose films.

The document FR 2 916 971 A1 discloses a slimming composition for application on the thighs including a bacterial cellulose substrate. The substrate includes at least 10% by weight of bacterial cellulose and an active substance. However, even at a very low thickness of only 1 mm, the article does not adhere to the skin without auxiliary measures. Particularly, the substrate should be used together with a support material so that it stays on the skin after application.

The document US 2011/0286948 A1 discloses a bacterial cellulose film that has a density gradient, wherein—when applied to the skin—the part of the film that is in contact with the skin surface has a lower density of microbial fibers than the side facing away from the skin surface. However, the bacterial cellulose film is produced using static fermentation.

The document WO 2007/091801 A1 discloses a bacterial cellulose sheet for use on the burned or otherwise wounded skin. The sheet has absorptive properties towards exudates. The sheet can be soaked with a solution of an active ingredient to obtain a sheet having from 0.5 to 10 mm thickness. The production process uses fruit juice as the cultivation medium. However, the production process is discontinuous and the moisture content of the finished product is very low.

The document US 2013/0244977 A1 teaches a bio-cellulose-containing mask that is produced in a cultivation medium containing ginseng extracts. The sheet is dried after preparation and then impregnated with a cosmetic emulsion. However, the bacterial cellulose is produced in a static process.

The document US 2009/0041815 A1 relates to a cosmetic composition comprising bacterial cellulose and a powder. A method is described in which the bacterial cellulose is brought into contact with the powder and afterwards applied to the skin. However, a support is needed for adhesion of the substrate to the skin. Moreover, the bacterial cellulose is produced using rotating disc fermentation. Such rotating disc fermentation, however, leads to bacterial cellulose having a tensile strength of even less than the bacterial cellulose produced using stationary conditions. The desired advantageous properties according to the present invention, however, are not met.

The document WO 2013/094077 A1 discloses a cosmetic sheet for lips comprising bacterial cellulose, water and at least one non-volatile oil. The sheet is supposed to remain on the lips for 10 seconds to 20 minutes. It is an object of the invention disclosed in that document that the sheet should adhere to the lips. However, treatment time is very short. Moreover, the bacterial cellulose is produced using a static production process, which makes production of the product very expensive, and comes along with further disadvantageous properties of the produced cellulose. It is mentioned that adhesive power of the sheet is sufficient because it contains water. However, this is only true if the thickness of the cosmetic sheet is low and the desired adhesion time is short. It is not disclosed in this document how much water or bacterial cellulose is used in the cosmetic sheet.

The document WO 2012/131623 A2 discloses a fractional cosmetic treatment using a laser and micro needles. It has to be acknowledged that such laser fracturing is a relatively specific treatment and is related to relatively specific needs. The fractional treatment is applied in order to reduce the barrier function of the skin. After fractional treatment an aqueous material is applied. However, the bacterial cellulose is produced in a static process and the use of a support, e.g. a textile wrap, is suggested.

Facial dermatitis, particularly perioral, periorbital, periocular or perinasal dermatitis, is a skin disease characterized by multiple small papules, pustules and vesicles which are localized to the perioral skin around the mouth, perinasal or nasolabial folds around the nostrils, or periocular area around the eyes, respectively. It most commonly affects women between the ages of 20 and 45 years, but may also affect children, men and the elderly. It is common, and has a tendency to recur in individuals who have had it once. Facial dermatitis may be asymptomatic, or may be associated with a burning, stinging sensation in the affected areas. The exact cause of the disease remains unknown. Following over-treatment, the skin is no longer able to produce the necessary fats and lipids, so that it is dry and scaly. The often considerably impaired appearance causes that the affected areas are more intensively treated and cared, and particularly moisturized, whereupon the rash becomes aggravated. Subjects suffering from facial dermatitis usually also increasingly apply cosmetics and skin-care products and, particularly, ointments and crèmes comprising cortisone. These cortisone products initially may achieve an improvement, but this is only short-lived. It is known in the art that the rash, despite further treatment with cortisone, is boosted and intensifies. For an effective treatment, the causes mentioned must be eliminated. In particular, the regular use of cosmetic creams ("moisturizers") should be avoided. In addition, phototherapy may be applied. During therapy, the affected skin areas may only be cleaned with water. For such treatment, particularly the above-described bio-cellular cellulose articles may be used, which however show the mentioned draw-backs.

SUMMARY OF THE INVENTION

It is an object of the present invention to provide an article and a medical, cosmetic or esthetic method which overcomes the above-described drawbacks.

It is a further object of the present invention to provide an article and a medical, cosmetic or esthetic method, wherein a subject's skin is provided with a soothing, cooling, caring, and alleviating effect to an area of skin by applying the article to the skin. It is a still further object of the present invention to provide an article and a medical, cosmetical or esthetical method, wherein the subject is able to move unimpededly while the article remains on the area of skin, wherein the article provides a moisturizing effect without wet feeling, wherein the article is lightweight and has very soft and smooth surface feel, wherein the article has an alleviating effect on skin that suffers from burns and/or all forms of dermatitis. Particularly, the article should be biodegradable and be produced by a very economical method.

It is a particular object of the present invention to provide an article and a medical, cosmetic or esthetic method useful in the medical treatment, or in the cosmetical or esthetical treatment, respectively, of skin diseases and skin conditions.

These and other problems are solved by the subject matter of the attached independent claims.

The above-described objects of the invention are achieved by an article containing biotechnologically produced nanostructured cellulose (BNC) for treating an area of skin, wherein the article comprises BNC in an amount of at least 1% by weight and at most 15% by weight, comprises fluid in an amount of at least 85% by weight and at most 99% by weight, has an average thickness of at least 0.5 mm and at most 8 mm, wherein the BNC is of a microbial origin and wherein the article has a polydispersity index of less than 30; or a method for treatment of an area of a subject's skin, comprising a. applying a cellulose-containing article to said area of skin, b. leaving the article on the skin for predetermined time period, c. removing the article from the skin, wherein the article comprises biotechnologically produced nanostructured cellulose (BNC) in an amount of at least 1% by weight and at most 15% by weight, comprises fluid in an amount of at least 85% by weight and at most 99% by weight, has an average thickness of at least 0.5 mm and at most 8 mm, and wherein the BNC is of microbial origin and the article has a polydispersity index of less than 3.0.

In a first aspect, the present invention provides a BNC-containing article for treating an area of skin according to the present invention, which comprises BNC in an amount of at least 1% by weight and at most 15% by weight, fluid in an amount of at least 85% by weight and at most 99% by weight, and which has an average thickness of at least 0.5 mm and at most 8 mm. The BNC contained in said article is of microbial origin.

In an embodiment, the present invention preferably provides a BNC-containing article for treating an area of skin according to the present invention, which consists of BNC in an amount of at least 1% by weight and at most 15% by weight, fluid in an amount of at least 85% by weight and at most 99% by weight, and which has an average thickness of at least 0.5 mm and at most 8 mm.

In a further aspect, the present invention provides a method for treatment of an area of a subject's skin. Said method comprises at least the steps of a. applying a BNC-containing article according to the present invention to said area of skin, b. leaving the article on the skin for a predetermined time period, c. removing the article from the skin.

The article of the present invention is particularly suitable for the use in the method of treatment according to the present invention. The various features, embodiments and advantages described in connection with the article may thus be also features, embodiments and advantages of the method, and vice versa.

The present invention considers particularly the application of the article in the treatment of various skin conditions, disorders or diseases: Particularly, said skin conditions, disorders or diseases may be selected from the group comprising dermatitis, particularly facial dermatitis, more particularly perioral, periorbital, periocular or perinasal dermatitis; dry skin; atopic dermatitis; burns; psoriasis; acne; rosacea and/or skin that has undergone photodynamic therapy. Thereby, the present inventive article and method is particularly useful in the treatment of dermatitis, particularly facial dermatitis, more particularly perioral, periorbital, periocular or perinasal dermatitis; dry skin; atopic dermatitis; burns; psoriasis; acne; rosacea and/or skin that has undergone photodynamic therapy. Particularly the treatment of dermatitis, particularly facial dermatitis, more particularly perioral, periorbital, periocular or perinasal dermatitis is considered herein.

The term "skin" in the sense of the present invention comprises the actual skin (comprising epidermis and dermis) as the outer covering of the body and additionally comprises mucous membranes, in particular nasal mucosa and/or oral mucosa. According to preferred embodiments of the present invention, the inventive article is applied subsequent to plastic surgery. In such embodiments, the article may support healing of the skin, in particular of the mucous membrane. In particularly preferred embodiments, the article is applied in rolled form, especially in form of a tamponade, particularly in form of a nasal tamponade.

The treatment according to the present invention may be a non-medical treatment, particularly a cosmetic or esthetic treatment; or a medical treatment.

Depending on the intended purpose, the article may comprise or may not comprise at least one active agent, particularly a pharmaceutically active agent and/or a naturally active agent and/or a cosmetically active agent and/or an esthetically active agent. In some embodiments, the article may comprise such active agent and may be used to apply and contact such active agent to the treated skin area. Preferably, such active agent is effective in the treatment of a skin condition or disorder or disease and/or useful in other dermatological uses.

Advantageously, such active agent may be introduced into the article, during the inventive method for treatment and/or during the inventive method of manufacturing: Such method may comprise a step of pre-treatment of the article with an active agent, preferably performed before application of a BNC-containing article to the skin. Particularly, the article may be immersed in a composition and/or fluid comprising the active agent, for example, a solution of fluid comprising the active agent, in an amount and time sufficient to enter the article, and, particularly, sufficient to release the active agent from the article to the skin during application in an effective amount, particularly a pharmaceutically and/or naturally and/or cosmetically and/or esthetically effective amount. The solution comprising the active agent preferably is a fluid-soluble solution. The uptake of the active agent from such solution into the article may be achieved by diffusion of the solution comprising the active agent into the article. However, additionally or alternatively, the article may be provided in a non-saturated form, i.e. having a fluid content below the maximum water absorption capacity of the article. Preferably, for such purpose, the article is provided having at least 1.5%, preferably at least 2%, more preferably at least 3%, still more preferably at least 4%, still more preferably at least 4.5%, still preferably at least 5% by weight, and most preferably at least 10% by weight of BNC. Providing the article with water content below the maximum water absorption capacity of the article advantageously increases the uptake efficiency of the active agent into the article, and reduces the amount of time, which is necessary for pre-treatment of the article with such active agent.

A pharmaceutically active agent, which may be comprised in the article, generally can be any pharmaceutically active agent suitable for the treatment of the respective skin condition, skin disorder or disease or dermatological use. Particularly, the pharmaceutically active agent may be advantageously selected from the group comprising azelaic acid, antiacarians, local anesthetics, e.g. lidocaine, corticoids, antimycotics, e.g. benzylamine or its derivatives, for example butenafine hydrochloride, immune suppressives, antibiotics, preferably tetracycline or minocycline, and particularly erythromycin or metronidazole, and wound caring products comprising wound-caring emulsions, e.g. cicalfate postacte, cold cream or antiseptical ointments, or the like. Particularly, steroids of class 1 or 2 may be advantageously applied. Pharmaceutically active agents, for ex-ample, erythromycin, azelaic acid, or metronidazole are particularly useful in the treatment of skin disorders or diseases and skin conditions, particularly facial dermatitis, for example perioral dermatitis and periorbital dermatitis, and may allow for a more rapid improvement. Corticoids are preferably avoided. However, also other pharmaceutically active agents may be comprised in the article. For example, antibiotics, particularly tetracycline and minocycline, can provide a therapy for inflammatory skin disorder or dis-eases or conditions, particularly of facial dermatitis. Such pharmaceutically active agents usually have to be applied repeatedly for several days or weeks.

The present invention allows for a relatively easy and comfortable way to apply an active agent, particularly pharmaceutically active agent, comprised in the article. Thereby, also other active agents are considered in the present invention comprising naturally, cosmetic and/or esthetic active agents, particularly of plant-based or herbal origin, for example from plant extracts and/or derivatives therefrom. A particularly preferred active agent is caffeine. The active agent may comprise at least one tanning agent or tannin. A tannin or tanning agent according to the present invention preferably is selected from the group comprising tea drugs, preferably selected from the group comprising cate-chines, pyrogallol-type tannins, and tannins of algae. Particularly, a tannin or tanning agent according to the present invention may be selected from the group comprising tannins of tannin-containing plants or plant parts, e.g. raspberry and/or blackberry leaves, oak tree, chestnut, acacia, lady's mantle (Alchemilla), witch-hazel leaves, grapes, black and green tea. For example, the article may comprise black tea and/or green tea and/or tanning agents of black tea and/or green tea, respectively. For this purpose, the article may be immersed in black and/or green tea before application. Tanning agents, particularly of black or green tea, may advantageously improve the skin condition, disorder or disease. In order to provide a sufficient amount of tanning agents, the tea is left to draw for at least 5 minutes, preferably at least 30 min, more preferably at least 60 min. Subsequently, the tea can be cooled and the article immersed in the tea, as heat may have a disadvantageous effect on inflammation.

In some embodiments in which the treatment is a medical treatment the method may comprise a step of applying photodynamic therapy to the area of skin. Particularly, applying the BNC-containing article to the area of skin may be carried out before and/or after the photodynamic therapy is applied. Preferably, the BNC-containing article is applied to the area of skin at least after applying photodynamic therapy. This advantageously allows for reduction of undesired side-effects of photodynamic therapy, and more particularly provides moisture and cooling to the treated area of skin. Preferably, the photodynamic therapy according to the present invention is a photodynamic therapy other than laser fracturing. Such photodynamic therapy may particularly be useful in the treatment of skin conditions, diseases and disorders, particularly of psoriasis, acne, actinic keratosis or rosacea. The present invention thus provides an advantageous use of the inventive article in the accompanying therapy of skin conditions, diseases and dis-orders of dermatological products or treatments.

In some embodiments in which the treatment is a non-medical treatment, the method may comprise an esthetic or cosmetic treatment, for example for wrinkle reduction. Particularly, the method may comprise a step of esthetic or cosmetic treatment, prefer-ably selected from the group comprising subcutaneous injection of hyaluronic acid and calcium hydroxylapatite (filler) or botulinum toxin (Botox), applying needling (for example micro-needling), peeling (for example fruit acid peeling), abrasion or laser fractioning to the area of skin. Particularly, applying the BNC-containing article to the area of skin may be carried out before and/or after the esthetic or cosmetic treatment is applied.

Preferably, the BNC-containing article is applied to the area of skin at least after applying an esthetic or cosmetic treatment. This advantageously allows for reduction of undesired side-effects of the esthetic or cosmetic treatment, for example swelling, and more particularly provides moisture and cooling to the treated area of skin.

The article can be advantageously designed such that its shape is adapted to the desired area of skin. In a preferred embodiment, the article is applied to the face or part of the face, e.g. the lid or rim of the eye, as the area of skin. The article can be provided in the form of a sheet, particularly a pad, preferably in the form of a mask, compress, bandage, dressing or patch or pads depending on the desired area of skin. This allows for a relatively easy application and provides an advantageous adaption on the skin. Preferably, the article is provided in the form of a face mask, mouth mask, forehead mask, eye mask or eye pads.

A "face mask" as used herein, preferably is dimensioned to cover essentially the entire skin of the face of a subject. A "mouth mask" as used herein, preferably is dimensioned to cover essentially the entire skin of the lower part of the face of a subject, particularly comprising mouth, cheeks, chin, and optionally a part of the throat. A "forehead mask" as used herein, preferably is dimensioned to cover essentially the entire skin of the forehead of the face of a subject, however, preferably not the eyes. An "eye mask" as used herein, preferably is dimensioned to cover essentially both eyes of a subject, and optionally at least the upper part of the nose. An "eye pad" as used herein, preferably is dimensioned to cover essentially one single eye of a subject. The term "eye pad" as used herein, preferably, refers to one particular dimension, i.e. adapted to cover essentially one single eye of a subject. However, the article in the form of an eye pad is not restricted to said particular form of use. More particularly, the present inventors have found that an article with the dimensioning and form of an eye pad as described herein, advantageously may also be applied, particularly without any further modification, to the corner area of the mouth. Insofar, it is to be understood that the term "eye pad" may additionally provide the advantageous application of the article at the corner area of the mouth.

The article according to the present invention is of particular advantage as it may be designed or provided such that it is self-adhering. Particularly, it adheres to the skin without any fixation means. Particularly, the article of the present invention can be designed relatively light weight and/or relatively small.

If it is referred herein to a "weight" or "weight per unit area", the "weight" or "weight per unit area", respectively, is preferably determined based on the mass of the article, or mass per unit area of the article, respectively. Said mass of the article, or mass per unit area of the article, respectively, is preferably determined in a wet state of the article, which is achieved by hot pressing of the article until a cellulose content of 3-4% is reached, and subsequently the mass of the article is determined.

The article of the present invention may preferably have a weight per unit area of at least 0.01 $g/cm^2$, preferably of at least 0.03 $g/cm^2$, more preferably at least 0.04 $g/cm^2$, still more preferably at least 0.05 $g/cm^2$. The article of the present invention may preferably have a weight per unit area of at most 1.00 $g/cm^2$, preferably of at most 0.30 g/cm2, more preferably at most 0.25 $g/cm^2$, still more preferably at most 0.20 $g/cm^2$, still more preferably at most 0.175 $g/cm^2$, and most preferably at most 0.170 $g/cm^2$. Particularly, the article of the present invention may preferably have a weight per unit area of from at least 0.01 $g/cm^2$ to at most 1.00 $g/cm^2$, more preferably from at least 0.01 $g/cm^2$ to at most 0.30 $g/cm^2$, still more preferably from at least 0.01 $g/cm^2$ to at most 0.25 $g/cm^2$, still more preferably from at least 0.01 $g/cm^2$ to at most 0.20 $g/cm^2$, still more preferably from at least 0.01 $g/cm^2$ to at most 0.175 $g/cm^2$, still more preferably from at least 0.01 $g/cm^2$ to at most 0.170 $g/cm^2$, still more preferably from at least 0.03 $g/cm^2$ to at most 1.00 $g/cm^2$, still more preferably from at least 0.03 $g/cm^2$ to at most 0.30 $g/cm^2$, still more preferably from at least 0.03 $g/cm^2$ to at most 0.25 $g/cm^2$, still more preferably from at least 0.03 $g/cm^2$ to at most 0.20 $g/cm^2$, still more preferably from at least 0.03 $g/cm^2$ to at most 0.175 $g/cm^2$, still more preferably from at least 0.03 $g/cm^2$ to at most 0.170 $g/cm^2$, still more preferably from at least 0.04 $g/cm^2$ to at most 1.00 $g/cm^2$, still more preferably from at least 0.04 $g/cm^2$ to at most 0.30 $g/cm^2$, still more preferably from at least 0.04 $g/cm^2$ to at most 0.25 $g/cm^2$, still more preferably from at least 0.04 $g/cm^2$ to at most 0.20 $g/cm^2$, still more preferably from at least 0.04 $g/cm^2$ to at most 0.175 $g/cm^2$, still more preferably from at least 0.04 $g/cm^2$ to at most 0.170 $g/cm^2$, still more preferably from at least 0.05 $g/cm^2$ to at most 1.00 $g/cm^2$, still more preferably from at least 0.05 $g/cm^2$ to at most 0.30 $g/cm^2$, still more preferably from at least 0.05 $g/cm^2$ to at most 0.25 $g/cm^2$, still more preferably from at least 0.05 $g/cm^2$ to at most 0.20 $g/cm^2$, still more preferably from at least 0.05 $g/cm^2$ to at most 0.175 $g/cm^2$, and most preferably from at least 0.05 g/cm2 to at most 0.170 $g/cm^2$. Such densities support the self-adhering properties of the article. If the density is very high, gravitational forces may exceed self-adhering forces. However, if the density is very low, the drapability of the article may be deteriorated. Drapability in the sense of the present invention is the ability of the article to be deformed and placed in a desired position without creation of unwanted creases or folds. The reason for deterioration of drapability at low densities of the article is that the self-adhering forces may be very strong making it very difficult or even impossible to put the article into an adequate position without creating unwanted creases or even tearing the article apart.

The width of an article of the present invention in the form of a face mask preferably is at least 175 mm, preferably at least 180 mm, more preferably at least 185 mm. The width preferably is at most 280 mm, more preferably at most 270 mm, still more preferably at most 250 mm, preferably at most 240 mm. The width preferably is at least 175 mm to at most 280 mm, more preferably at least 175 mm to at most 270 mm, still more preferably at least 175 mm to at most 250 mm, still more preferably at least 175 mm to at most 240 mm, still more preferably at least 180 mm to at most 280 mm, still more preferably at least 180 mm to at most 270 mm, still more preferably at least 180 mm to at most 250 mm, still more preferably at least 180 mm to at most 240 mm, still more preferably at least 185 mm to at most 280 mm, still more preferably at least 185 mm to at most 270 mm, still more preferably at least 185 mm to at most 250 mm, and still more preferably at least 185 mm to at most 240 mm.

The article of the present invention in the form of a face mask preferably has a height of at least 170 mm, preferably at least 175 mm. The height is preferably at most 200 mm, preferably at most 180 mm, more preferably at most 175 mm. The height is preferably from at least 170 mm to at most 200 mm, more preferably from at least 170 mm to at most 180 mm, still more preferably from at least 170 mm to at most 175 mm, still more preferably from at least 175 mm to at most 200 mm, still more preferably from at least 175 mm to at most 180 mm, and still more preferably from at least 175 mm to at most 175 mm.

The width-to-height ratio of the article of the present invention in the form of a face mask preferably is of at least 1.000, preferably of at least 1.050, more preferably of at least 1.057. The width-to-height ratio of the article of the present invention in the form of a face mask preferably is of at most 1.500, more preferably of at most 1.450, still more preferably of at most 1.425, and most preferably of at most 1.412. The width-to-height ratio of the article of the present invention in the form of a face mask preferably is from at least 1.000 to at most 1.500, more preferably from at least 1.000 to at most 1.450, still more preferably from at least 1.000 to at most 1.425, still more preferably from at least 1.000 to at most 1.412, still more preferably from at least 1.050 to at most 1.500, still more preferably from at least 1.050 to at most 1.450, still more preferably from at least 1.050 to at most 1.425, still more preferably from at least 1.050 to at most 1.412, still more preferably from at least 1.057 to at most 1.500, still more preferably from at least 1.057 to at most 1.450, still more preferably from at least 1.057 to at most 1.425, and most preferably from at least 1.057 to at most 1.412. Such ratios are advantageous for fitting the article to the face and for improving the self-adhering properties of the article. If the ratio is very high, the article only fits poorly to the face. However, if the ratio is very low, self-adherence of the article to the skin is impaired. In summary, an adequate width-to-height ratio as described above is advantageous for handling, adhesion and fitting of the article.

The article of the present invention in the form of a face mask preferably has a total weight of at most 120 g, preferably at most 80 g, more preferably at most 70 g, still more preferably at most 68.5 g, still more preferably at most 50 g, still more preferably at most 40 g, still more preferably at most 30 g, and still more preferably at most 28 g.

The article of the present invention in the form of a face mask may preferably have a weight per unit area of at least 0.03 g/cm$^2$, preferably at least 0.04 g/cm$^2$, more preferably at least 0.05 g/cm$^2$. The article of the present invention in the form of a face mask may preferably have a weight per unit area of at most 0.25 g/cm$^2$, preferably at most 0.20 g/cm$^2$, more preferably at most 0.17 g/cm$^2$. The article of the present invention in the form of a face mask may preferably have a weight per unit area of from at least 0.03 g/cm$^2$ to at most 0.25 g/cm$^2$, more preferably from at least 0.03 g/cm$^2$ to at most 0.20 g/cm$^2$, still more preferably from at least 0.03 g/cm$^2$ to at most 0.17 g/cm$^2$, still more preferably from at least 0.04 g/cm$^2$ to at most 0.25 g/cm$^2$, still more preferably from at least 0.04 g/cm$^2$ to at most 0.20 g/cm$^2$, still more preferably from at least 0.04 g/cm$^2$ to at most 0.17 g/cm$^2$, still more preferably from at least 0.05 g/cm$^2$ to at most 0.25 g/cm$^2$, still more preferably from at least 0.05 g/cm$^2$ to at most 0.20 g/cm$^2$, and most preferably from at least 0.05 g/cm$^2$ to at most 0.17 g/cm$^2$.

In a particular preferred embodiment, an article of the present invention in the form of a face mask has an average thickness of about 2 mm, and a width of about 185 mm, and a height of about 175 mm, and a weight of about 53 g, and a weight per unit area of from at least 0.14 g/cm$^2$ to at most 0.17 g/cm$^2$. In a further particular preferred embodiment an article of the present invention in the form of a face mask has an average thickness of about 0.8 to 1.0 mm, and a width of about 185 mm, and a height of about 175 mm, and a weight of about 27 g, and a weight per unit area of from at least 0.05 g/cm$^2$ to at most 0.11 g/cm$^2$. In another preferred embodiment an article of the present invention in the form of a face mask has an average thickness of about 1.5 to 2.5 mm, and a width of about 250 mm, and a height of about 200 mm, and an average weight of about 106 g, and a weight per unit area of from at least 0.19 g/cm$^2$ to at most 0.25 g/cm$^2$. The indicated weight refers to articles having a fluid content of 95% by weight.

The width of an article of the present invention in the form of a mouth mask preferably is at least 100 mm, preferably at least 110 mm, more preferably at least 120 mm, most preferably at least 125 mm. The width preferably is at most 135 mm, preferably at most 130 mm, more preferably at most 125 mm. The width preferably is at least 100 mm to at most 135 mm, more preferably at least 100 mm to at most 130 mm, more preferably at least 100 mm to at most 125 mm, still more preferably at least 110 mm to at most 135 mm, at least 110 mm to at most 130 mm, and still more preferably at least 120 mm to at most 130 mm. The article of the present invention in the form of a mouth mask preferably has a height of at least 75 mm, preferably at least 80 mm, more preferably at least 85 mm. The height is preferably at most 95 mm, more preferably at most 90 mm, still more preferably at most 85 mm. The width-to-height ratio of the article of the present invention in the form of a mouth mask preferably is of at least 1.25, more preferably at least 1.30, still more preferably at least 1.35, still more preferably at least 1.40, still more preferably at least 1.45, and most preferably at least 1.47. The width-to-height ratio of the article of the present invention in the form of a mouth mask preferably is of at most 1.60, more preferably at most 1.55, still more preferably at most 1.50, and most preferably at most 1.47. The width-to-height ratio of the article of the present invention in the form of a mouth mask preferably is from at least 1.25 to at most 1.60, more preferably from at least 1.25 to at most 1.55, still more preferably from at least 1.25 to at most 1.50, still more preferably from at least 1.25 to at most 1.47, still more preferably from at least 1.30 to at most 1.60, still more preferably from at least 1.30 to at most 1.55, still more preferably from at least 1.30 to at most 1.50, still more preferably from at least 1.30 to at most 1.47, still more preferably from at least 1.35 to at most 1.60, still more preferably from at least 1.35 to at most 1.55, still more preferably from at least 1.35 to at most 1.50, still more preferably from at least 1.35 to at most 1.47, still more preferably from at least 1.40 to at most 1.60, still more preferably from at least 1.40 to at most 1.55, still more preferably from at least 1.40 to at most 1.50, still more preferably from at least 1.40 to at most 1.47, still more preferably from at least 1.45 to at most 1.60, still more preferably from at least 1.45 to at most 1.55, still more preferably from at least 1.45 to at most 1.50, still more preferably from at least 1.45 to at most 1.47, still more preferably from at least 1.47 to at most at most 1.60, still more preferably from at least 1.47 to at most at most 1.55, and most preferably from at least 1.47 to at most 1.50. The article of the present invention in the form of a mouth mask preferably has a total weight of at most 25 g, preferably at most 20,5 g, more preferably at most 15 g, still more preferably at most 10 g, still more preferably at most 8 g, and still more preferably at most 7.8 g. The article of the present invention in the form of a mouth mask may preferably have a weight per unit area of at least 0.03 g/cm$^2$, preferably at least 0.04 g/cm$^2$, more preferably at least 0.05 g/cm$^2$, still more preferably at least 0.06 g/cm$^2$. The article of the present invention in the form of a mouth mask may preferably have a weight per unit area of at most 0,5 g/cm$^2$, preferably at most 0.4 g/cm$^2$, more preferably at most 0.3 g/cm$^2$, still more preferably at most 0.25 g/cm$^2$. The article of the present invention in the form of a mouth mask may preferably have a weight per unit area of from at least 0.03 g/cm² to at most 0,5 g/cm², more preferably from at least 0.04 g/cm² to at most 0,5 g/cm², still more preferably from at least 0.05 g/cm² to at most 0,5 g/cm², still more preferably from at least 0.06 g/cm² to at most 0,5 g/cm², still more preferably from at least 0.03 g/cm² to at most 0.4 g/cm², still more preferably from at least 0.04 g/cm², to at most 0.4 g/cm², still more preferably from at least 0.05 g/cm² to at most 0.4 g/cm², still more preferably from at least 0.06 g/cm² to at most 0.4 g/cm², still more preferably from at least 0.03 g/cm² to at most 0.3 g/cm², still more preferably from at least 0.04 g/cm², to at most 0.3 g/cm², still more preferably from at least 0.05 g/cm² to at most 0.3 g/cm², still more preferably from at least 0.06 g/cm² to at most 0.3 g/cm², still more preferably from at least 0.03 g/cm² to at most 0.25 g/cm², still more preferably from at least 0.04 g/cm², to at most 0.25 g/cm², still more preferably from at least 0.05 g/cm² to at most 0.25 g/cm², and most preferably from at least 0.06 g/cm² to at most 0.25 g/cm². In a particular preferred embodiment, an article of the present invention in the form of a mouth mask has an average thickness of about 2 mm, and a width of about 125 mm, and a height of about 85 mm, and a weight of about 20 g and a weight per unit area of from at least 0.175 g/cm² to at most 0.215 g/cm².

In a further particular preferred embodiment an article of the present invention in the form of a mouth mask has an average thickness of about 1.0 mm, and a width of about 125 mm, and a height of about 85 mm, and a weight of about 7.65 g and a weight per unit area of from at least 0.060 g/cm² to at most 0.085 g/cm². The width of an article of the present invention in the form of a forehead mask preferably is of at least 175 mm, preferably of at least 180 mm, more preferably of at least 185 mm, most preferably of at least 190 mm. The width preferably is of at most 200 mm, preferably of at most 195 mm, more preferably of at most 190 mm. The width preferably is of at least 175 mm to at most 200 mm, more preferably of at least 175 mm to at most 195 mm, more prefer-ably at least 175 mm to at most 190 mm, still more preferably of at least 185 mm to at most 200 mm, of at least 185 mm to at most 195 mm, and still more preferably of at least 185 mm to at most 190 mm. The article of the present invention in the form of a forehead mask preferably has a height of at least 50 mm, preferably at least 55 mm, more preferably at least 60 mm. The height is preferably at most 70 mm, more prefer-ably at most 65 mm, still more preferably at most 60 mm. The width-to-height ratio of the article of the present invention in the form of a forehead mask preferably is of at least 3.1 and at most 3.2. The article of the present invention in the form of a forehead mask preferably has a total weight of at most 25 g, preferably at most 22.5 g, more preferably at most 21 g, still more preferably at most 15 g, still more preferably at most 12.5 g, and still more preferably at most 11 g.

The article of the present invention in the form of a forehead mask may preferably have a weight per unit area of at least 0.050 g/cm², more preferably at least 0.060 g/cm2, still more preferably at least 0.070 g/cm², and most preferably at least 0.080 g/cm2. The article of the present invention in the form of a forehead mask may preferably have a weight per unit area of at most 0.300 g/cm², more preferably at most 0.250 g/cm², still more preferably at most 0.200 g/cm², and most preferably at most 0.190 g/cm². The article of the present invention in the form of a forehead mask may preferably have a weight per unit area of from at least 0.050 g/cm² to at most 0.300 g/cm², more preferably from at least 0.050 g/cm² to at most 0.250 g/cm², still more preferably from at least 0.050 g/cm² to at most 0.200 g/cm², still more preferably from at least 0.050 g/cm² to at most 0.190 g/cm², still more preferably from at least 0.060 g/cm² to at most 0.300 g/cm², still more preferably from at least 0.060 g/cm² to at most 0.250 g/cm², still more preferably from at least 0.060 g/cm² to at most 0.200 g/cm2, still more preferably from at least 0.060 g/cm² to at most 0.190 g/cm², still more preferably from at least 0.070 g/cm² to at most 0.300 g/cm², still more preferably from at least 0.070 g/cm² to at most 0.250 g/cm2, still more preferably from at least 0.070 g/cm² to at most 0.200 g/cm², still more preferably from at least 0.070 g/cm² to at most 0.190 g/cm², still more preferably from at least 0.080 g/cm² to at most 0.300 g/cm², still more preferably from at least 0.080 g/cm² to at most 0.250 g/cm², still more preferably from at least 0.080 g/cm² to at most 0.200 g/cm2, and most preferably from at least 0.080 g/cm² to at most 0.190 g/cm².

In a particular preferred embodiment, an article of the present invention in the form of a forehead mask has an average thickness of about 2 mm, and a width of about 190 mm, and a height of about 60 mm, and a weight of about 20.0 g and a weight per unit area of from at least 0.170 g/cm² to at most 0.190 g/cm².

In a further particular preferred embodiment an article of the present invention in the form of a forehead mask has an average thickness of about 1.0 mm, and a width of about 190 mm, and a height of about 60 mm, and a weight of about 10.75 g and a weight per unit area of from at least 0.080 g/cm² to at most 0.190 g/cm².

The width of an article of the present invention in the form of an eye mask preferably is at least 185 mm, preferably at least 188 mm, more preferably at least 190 mm, most preferably at least 191 mm. The width preferably is at most 195 mm, preferably at most 192.5 mm, more preferably at most 191 mm. The width preferably is at least 185 mm to at most 195 mm, more preferably at least 185 mm to at most 192.5 mm, more preferably at least 185 mm to at most 191 mm, still more preferably at least 190 mm to at most 195 mm, at least 190 mm to at most 192,5 mm, and still more preferably at least 191 mm to at most 192.5 mm. The article of the present invention in the form of an eye mask preferably has a height of at least 55 mm, preferably at least 57.5 mm, more preferably at least 60 mm. The height is preferably at most 65 mm, more preferably at most 62.5 mm, still more preferably at most 60 mm. The width-to-height ratio of the article of the present invention in the form of an eye mask preferably is of at least 3.15 and at most 3.25. The article of the present invention in the form of an eye mask preferably has a total weight of at most 25 g, preferably at most 22.5 g, more preferably at most 21 g, still more preferably at most 15 g, still more preferably at most 12.5 g, and still more preferably at most 11 g.

The article of the present invention in the form of an eye mask may preferably have a weight per unit area of at least 0.050 g/cm², more preferably at least 0.060 g/cm², still more preferably at least 0.070 g/cm², and most preferably at least 0.080 g/cm². The article of the present invention in the form of an eye mask may preferably have a weight per unit area of at most 0.400 g/cm², more preferably at most 0.350 g/cm², still more preferably at most 0.300 g/cm², and most preferably at most 0.250 g/cm². The article of the present invention in the form of a eye mask may preferably have a weight per unit area of from at least 0.050 g/cm² to at most 0.400 g/cm², more preferably from at least 0.050 g/cm2 to at most 0.350 g/cm², still more preferably from at least 0.050 g/cm² to at most 0.300 g/cm2, still more preferably from at least 0.050 g/cm² to at most 0.250 g/cm², still more preferably from at least 0.060 g/cm² to at most 0.400 g/cm², still more preferably from at least 0.060 g/cm2 to at most 0.350 g/cm², still more preferably from at least 0.060 g/cm² to at most 0.300 g/cm², still more preferably from at least 0.060 g/cm² to at most 0.250 g/cm², still more preferably from at least 0.070 g/cm² to at most 0.400 g/cm², still more preferably from at least 0.070 g/cm² to at most 0.350 g/cm², still more preferably from at least 0.070 g/cm² to at most 0.300 g/cm², still more preferably from at least 0.070 g/cm² to at most 0.250 g/cm², still more preferably from at least 0.080 g/cm2 to at most 0.400 g/cm², still more preferably from at least 0.080 g/cm² to at most 0.350 g/cm², still more preferably from at least 0.080 g/cm² to at most 0.300 g/cm², and most preferably from at least 0.080 g/cm² to at most 0.250 g/cm².

In a particular preferred embodiment, an article of the present invention in the form of an eye mask has an average thickness of about 2 mm, and a width of about 191 mm, and a height of about 60 mm, and a weight of about 23.20 g and a weight per unit area of from at least 0.175 g/cm2 to at most 0.250 g/cm2. In a further particular preferred embodiment an article of the present invention in the form of an eye mask has an average thickness of about 1.0 mm, and a width of about 190 mm, and a height of about 60 mm, and a weight of about 11.0 g and a weight per unit area of from at least 0.080 g/cm² to at most 0.110 g/cm². The width of an article of the present invention in the form of an eye pad preferably is of at least 67.5 mm, preferably of at least 70 mm, more preferably of at least 72.5 mm, most preferably of at least 75 mm. The width preferably is of at most 80 mm, preferably of at most 77.5 mm, more preferably of at most 75 mm. The width preferably is of at least 67.5 mm to at most 80 mm, more preferably of at least 67.5 mm to at most 77.5 mm, more preferably at least 67.5 mm to at most 75 mm, still more preferably of at least 72.5 mm to at most 77.5 mm, of at least 72.5 mm to at most 75 mm. The article of the present invention in the form of an eye pad preferably has a height of at least 30 mm, preferably at least 32.5 mm, more preferably at least 35 mm. The height is preferably at most 40 mm, more preferably at most 37.5 mm, still more preferably at most 35 mm. The width-to-height ratio of the article of the present invention in the form of an eye pad preferably is of at least 2.1 and at most 2.2. The article of the present invention in the form of an eye pad preferably has a total weight of at most 3.5 g, preferably at most 3.0 g, more preferably at most 2.8 g, still more preferably at most 2.75 g.

The article of the present invention in the form of an eye pad may preferably have a weight per unit area of at least 0.055 g/cm², more preferably at least 0.065 g/cm², and most preferably at least 0.075 g/cm². The article of the present invention in the form of an eye pad may preferably have a weight per unit area of at most 0.120 g/cm², more preferably at most 0.135 g/cm², and most preferably at most 0.140 g/cm². The article of the present invention in the form of a eye pad may preferably have a weight per unit area of from at least 0.055 g/cm² to at most 0.120 g/cm², more preferably from at least 0.055 g/cm² to at most 0.135 g/cm², still more preferably from at least 0.055 g/cm² to at most 0.140 g/cm², still more preferably from at least 0.065 g/cm² to at most 0.120 g/cm², still more preferably from at least 0.065 g/cm² to at most 0.135 g/cm², still more preferably from at least 0.065 g/cm² to at most 0.140 g/cm², still more preferably from at least 0.075 g/cm² to at most 0.120 g/cm², still more preferably from at least 0.075 g/cm² to at most 0.135 g/cm², and most preferably from at least 0.075 g/cm² to at most 0.140 g/cm².

In a particular preferred embodiment, an article of the present invention in the form of an eye pad has an average thickness of about 1.0 to 2.0 mm, and a width of about 75 mm, and a height of about 35 mm, and a weight of about 2.75 g and a weight per unit area of from at least 0.140 g/cm² to at most 0.120 g/cm².

Terms like "height" or "width" of an article as used herein preferably refer to the largest respective expansion of the article in its position of intended use. For example, the terms "height" or "width" determine the respective largest expansion of the article, as if placed on the face of a subject. The term "width" of an article as used herein, preferably refers to the largest expansion of the article in lateral direction, e.g. from ear to ear, whereas the term "height" preferably refers to the largest expansion of the article in a position of its intended use in cranial-caudal direction.

Particularly, the inventive method for treatment in step a. may comprise adhering of the article to the skin by adhesion, and preferably without any fixation means. This allows a subject applying the article to move unimpededly while the article remains on the area of skin, even if the predetermined period of time is relatively long. It is the merit of the present inventors that the advantageous adhesion of an article according to the present invention is depending on a variety of parameters, rather than one parameter alone. Particularly, such parameters are the advantageous surface characteristics of the inventive article, the relatively low weight of the articles of the present invention, the advantageously high tensile strength, which allows a better adaption to the skin and face structures.

The present inventors have found that the article and the method for treatment of the present invention advantageously provides a soothing, cooling, caring, and alleviative effect to an area of skin by applying the article to the skin. Particularly, applying the article to the skin may reduce pain, skin irritation or spanning of the skin while the article remains on the area of skin and provides a moisturizing effect without wet feeling. Thereby the article and the method are particularly useful in the treatment of skin dis-eases, conditions and disorders, particularly all forms of dermatitis and more particularly in the treatment of facial dermatitis, e.g. perioral, periorbital, periocular or perinasal dermatitis; however, also of psoriasis, acne or rosacea. Advantageously, the article and the method of the present invention allow for reduction of the itchiness of the skin, and thus may reduce the desire of the subject to itch the area of the skin. Moreover, the article and the method of the present invention advantageously increase physical com-fort and self-adhering, which allows the subject to comfortably and freely move during application of the article to the area of skin. Still further the article and method advantageously reduces swellings and skin redness, and erythema.

The inventive article and method may in general be applied to any subject in need thereof, particularly a subject suffering from a skin disease, disorder or condition. However, preferably the subject is a mammal, in particular a human, preferably a human female.

According to the inventive method for treatment the article is left on the skin for a pre-determined time period. To achieve the desired advantageous effects it is preferred that the time period is not too short. The predetermined time period preferably is at least 10 minutes, at least 15 minutes, at least 20 minutes, at least 30 minutes, at least 1 hour, at least 2 hours, or at least 3 hours. However, in order to prevent discomfort or effects of over-use, it is preferred that the time period is not too long. The predetermined time period preferably is at most 12 hours, preferably at most 10 hours, more preferably at most 8 hours, still more preferably at most 5 hours, or still more preferably at most 4 hours. In connection therewith, a person skilled in the art will immediately understand that an article having higher fluid content may provide moisture in general for a longer time period. Thereby, a higher water absorption capacity (WAC) is preferred, which in general allows for a longer time period of efficient application.

A particularly advantageous effect may be achieved, if the article is applied or the method is performed repeatedly for a treatment interval. A continuously repeated application is of advantage in order to achieve and improve the positive effects on the skin. Thereby it is preferred that in a treatment interval steps a. to c., and optionally a step of pre-treatment of the article, of the method for treatment are performed at least once within 24 hours. In an embodiment the treatment interval is at least 1 day, at least 2 days, at least 3 days or at least 4 days. It is particularly preferred that during said treatment interval the subject does not apply cosmetics and skin-care products other than the product of the present invention. This may advantageously initiate and support the natural healing process. However, the treatment interval should also not be too long. Preferably, the treatment interval is up to 1 year, up to 6 months, up to 3 months, up to 1 month, up to 2 weeks or up to 1 week.

A particularly preferred application of the present invention in which photodynamic therapy is applied to the subject, it is preferred that the steps a. to c., and optionally a step of pre-treatment of the article, of the inventive method are performed for a first time at most 1 hour after a step of applying photodynamic therapy to the area of skin, wherein the predetermined time period is from at least 30 min to at most 60 min; and additionally and subsequently, the steps a. to c., and optionally a step of pre-treatment of the article, are performed at least once within 24 hours during a treatment interval of at least 5 days and at most 7 days, wherein the predetermined time period is from at least 3 hours to at most 4 hours. It is known in the art that patients which are subjected to photodynamic therapy usually do not suffer from pain during the application of photodynamic therapy. However, the burning effects of the treatment usually appear on the day after the photodynamic therapy treatment. With the article of the present invention applied to a subject for a first time at most 1 hour after a step of applying photodynamic therapy the burning effects due to the photodynamic therapy treatment can advantageously be reduced, already in advance.

Such scheme of application is particularly useful and effective, as the first application of the product within one hour after photo-therapy treatment allows an immediate effect of the inventive product. The further applications of the product additionally and subsequent to said first application can advantageously be performed without help or supervision of a medical professional, particularly by the subject itself.

The article of the present invention is particularly advantageous as it is of relatively light weight and has very soft and smooth surface feel. Particularly, the article provides an alleviating effect on skin that suffers from skin diseases, disorders and conditions, particularly burns and all forms of dermatitis. Moreover, the article advantageously is biodegradable and can be produced by a very economical method.

In a still further aspect the above described problems are also advantageously solved by a method of manufacturing a BNC-containing article according to the present invention.

In connection therewith it is important to understand that the method of manufacturing of the article according to the present invention shows a strong influence on various parameters of the article, which particularly also influence the efficacy of treatment and provides its advantageous properties. Particularly, the method of manufacturing may have an impact on the fibers of the BNC and their average diameter, the sum of the constituents fluid and BNC, the mass ratio of BNC Iα to BNC Iβ, the volumetric mass density, the molecular mass, the amount of carbonyl groups, the polydispersity index ($M_w/M_n$), the crystallinity Ic, the water absorption capacity, the water retention capacity and/or the tensile strength of the BNC, and of the BNC-containing article, respectively.

The method of manufacturing comprises at least the following steps: a.) providing BNC in a continuous semi-static process, b.) providing the article according to the present invention; and c.) optionally sterilizing the article.

Particularly, a step a) of providing BNC in a continuous semi-static process may comprise providing the BNC as a BNC fleece. The terms "fleece" and "non-woven" are used interchangeably in the present description. Particularly, step b.) of providing the article according to the present invention may comprise a step of cutting the article, in particular with a jet of fluid into form, e.g. eye pad, forehead mask, eye mask, face mask, or the like. The fluid jet preferably is provided with a pressure of at least 1000 and at most 4000 bar. The fluid jet preferably has a diameter of from 100 μm to 300 μm, more preferably of from 125 μm to 200 μm, most preferably of about 150 μm. Such cutting with a fluid jet is advantageous compared to cutting methods usually provided in the art, for example, thermal cutting with a laser or the like, or mechanical cutting. Such methods of the prior art usually compromise the structure of the BNC material. The cutting ac-cording to the present invention, however, provides a high quality of the cutting edge without destruction of the surrounding BNC.

The method of manufacturing according to the present invention optionally comprises a step c.) of sterilizing the article. Said sterilizing step preferably comprises application of beta-irradiation, for example e-beam. This is advantageous as the number of radicals, which usually are generated using gamma-irradiation applied in the art, are not formed or reduced. This is particularly the case, as the application of beta-irradiation may allow for shorter treatment.

The method of manufacturing of the article according to the present invention comprises a continuous semi-static process of providing biotechnologically produced nano-structured cellulose (BNC). It is particularly preferred that the BNC is not produced in a static or discontinuous process. A "continuous semi-static" process as used herein, preferably refers to a method in which the BNC is produced from a bacterial culture in a cultivation medium, which is not actively stirred, shacked, or otherwise moved during BNC synthesis, in which, however, the BNC is continuously produced by the bacterial culture. The fact that the cultivation medium is not actively stirred, shacked, or other-wise moved during BNC synthesis does neither exclude harvesting or removal of BNC from the bacterial culture and/or reaction vessel during BNC synthesis nor adding cultivation medium and/or constituents of the cultivation medium during BNC biosynthesis. Particularly, in a "continuous semi-static" process as used herein, preferably the BNC is harvested or removed from the bacterial culture and/or reaction vessel more than once during BNC synthesis, particularly regularly, step-wise and/or continuously. Particularly, in a "continuous semi-static" process as used herein, preferably the cultivation medium and/or constituents of the cultivation medium are added more than once, preferably regularly, step-wise and/or continuously during the BNC synthesis. In connection therewith a "continuous semi-static" process as used herein, preferably is not a batch production method.

In an embodiment of the "continuous semi-static" process, up to 1 m², preferably up to 2.5 m², more preferably up to 5 m² of BNC is harvested or removed from the bacterial culture and/or reaction vessel per day, particularly regularly, step-wise and/or continuously.

The advantageous properties and features, for example the advantageous adhesion properties or relatively light weight, of the article, of this invention, particularly of the BNC content of the article, can be adjusted by choosing suitable culturing conditions. The BNC content of the article according to the present invention preferably is produced in the form of a BNC fleece.

Particularly, step a) of providing BNC in a continuous semi-static process may comprise at least one of the following steps:
- a') providing a reaction vessel comprising cultivation medium;
- a") inoculating the cultivation medium with a BNC-producing bacterial strain; and/or
- a''') bacterial synthesis of BNC in the reaction vessel.

Production of the BNC can preferably be done at a cell count of from $10^4$ to $10^7$ cells/ml of culturing medium during the culturing. Preferably, a step a") of inoculating the cultivation medium with a BNC-producing bacterial strain comprises providing a stock culture having about $10^6$ cells/ml and inoculating the cultivation medium with the stock culture resulting in a cell concentration of about $5 \times 10^3$ cells/ml. The properties of the obtained BNC content of the article may also be influenced by the volume ratio of the cultivation medium to the bacterial strain stock culture used for inoculation. Preferably, the volume ratio is at least 2:1, more preferably at least 5:1, more preferably at least 10:1, and more preferably at least 15:1. Preferably, the volume ratio is at most 50:1, more preferably at most 30:1, and more preferably at most 20:1.

Preferably, at least step a''') of bacterial synthesis of BNC comprises adding cultivation medium, or preferably selectively adding ingredients of the cultivation medium, into the reaction vessel more than once, preferably regularly, step-wise and/or continuously during BNC synthesis. Particularly, at least step a''') of bacterial synthesis of BNC in the reaction vessel preferably comprises incubating a bacterial culture in a cultivation medium, which is not actively stirred, shacked, or otherwise moved during BNC synthesis. The fact that the cultivation medium is not actively stirred, shacked, or otherwise moved during BNC synthesis does neither exclude harvesting or removal of BNC from the bacterial culture and/or reaction vessel during BNC synthesis nor adding cultivation medium and/or constituents of the cultivation medium during BNC biosynthesis. Additionally or alternatively, at least step a''') of bacterial synthesis of BNC in the reaction vessel preferably comprises continuously producing BNC. Additionally or alternatively, at least step a''') of bacterial synthesis of BNC in the reaction vessel preferably comprises harvesting and/or removing BNC from the bacterial culture and/or reaction vessel during BNC syn-thesis more than once, preferably regularly, step-wise and/or continuously during BNC synthesis. Additionally or alternatively, at least step a''') of bacterial synthesis of BNC in the reaction vessel preferably comprises adding cultivation medium and/or constituents of the cultivation medium to the bacterial culture and/or reaction vessel more than once, preferably regularly, step-wise and/or continuously during the BNC synthesis.

The properties of the obtained BNC content of the article may also be influenced by the composition of the cultivation medium. Preferably, the cultivation medium comprises a carbon source, a nitrogen source and a vitamin source and optionally a buffer system. Preferably, the carbon source is selected from one or more sugars and their derivatives. Preferably, the nitrogen source is peptone. Preferably, the vitamin source is yeast extract. Preferably, the buffer system is disodium hydrogen phosphate and citric acid.

Preferably, the cultivation medium is liquid.

Preferably, the cultivation medium comprises the carbon source in an amount of least 10 g/l, more preferably at least 15 g/l based on the volume of the cultivation medium. Preferably, the cultivation medium comprises the carbon source in an amount of at most 30 g/l, more preferably at most 25 g/l based on the volume of the cultivation medium. Particularly preferably, the cultivation medium comprises the carbon source in an amount of about 20 g/l.

Preferably, the cultivation medium comprises the nitrogen source in an amount of least 2 g/l, more preferably at least 4 g/l based on the volume of the cultivation medium. Preferably, the cultivation medium comprises the nitrogen source in an amount of at most 10 g/l, more preferably at most 7 g/l based on the volume of the cultivation medium. Particularly preferably, the cultivation medium comprises the nitrogen source in an amount of about 5 g/l.

Preferably, the cultivation medium comprises the vitamin source in an amount of least 2 g/l, more preferably at least 4 g/l based on the volume of the cultivation medium. Preferably, the cultivation medium comprises the vitamin source in an amount of at most 10 g/l, more preferably at most 7 g/l based on the volume of the cultivation medium. Particularly preferably, the cultivation medium comprises the vitamin source in an amount of about 5 g/l.

Preferably, the cultivation medium comprises the buffer system in an amount of least 2 g/l, more preferably at least 4 g/l based on the volume of the cultivation medium. Preferably, the cultivation medium comprises the buffer system in an amount of at most 10 g/l, more preferably at most 5 g/l based on the volume of the cultivation medium. Particularly preferably, the cultivation medium comprises the buffer system in an amount of about 4.5 g/l.

Particularly, the cultivation medium comprises 20 g/l glucose, 5 g/l peptone, 5 g/l yeast extract, 3.4 g/l disodium hydrogen phosphate and 1.15 g/l citric acid.

Particularly, the cultivation medium is free of ginseng extracts.

The properties of the obtained BNC content of the article may also be influenced by the cultivation temperature. Preferably, the cultivation temperature is at least 20° C., more preferably at least 25° C., more preferably at least 28° C. If the cultivation temperature is too low, the bacterial strains do not grow properly. Preferably, the cultivation temperature is at most 36° C., more preferably at most 33° C., more preferably at most 30° C. If the cultivation temperature is too high, the bacterial strains do not grow properly.

The properties of the obtained BNC content of the article may also be influenced by the cultivation time. Preferably the cultivation time is at least 1 day, more preferably at least 3 days, still more preferably at least 7 days, and still more preferably at least 10 days. If the cultivation time is too short, not enough cellulose is produced. Preferably, the cultivation time is at most 1 year, more preferably at most 6 month, still more preferably at most 30 days, still more preferably at most 25 days, and still more preferably at most 20 days. Particularly, a semi-static continuous process as described herein, may allow for advantageously long cultivation times, during which, more preferably the BNC is harvested or removed from the bacterial culture and/or reaction vessel more than once during BNC synthesis, particularly regularly, step-wise and/or continuously.

The properties of the obtained BNC content of the article may also be influenced by the culture volume. Preferably, the culture volume is at least 20 ml, more preferably at least 500 ml, still more preferably at least 2000 ml, still more preferably at least 4000 ml, and still more preferably at least 10,000 ml. Preferably, the culture volume is at most 200 l, more preferably at most 180 l, more preferably at most 100 l, and still more preferably at most 50 l. Particularly, the semi-static continuous process as described herein may allow for advantageously high culture volumes.

The culture volumes particularly may also depend on the desired BNC synthesis area, and vice versa. The properties of the obtained BNC content of the article may also be influenced by the cultivation vessel and/or synthesis area. Preferably, the cultivation vessel has a synthesis area of at least 1 cm$^2$, more preferably at least 10 cm$^2$, more preferably at least 100 cm$^2$, and still more preferably at least 10 m$^2$. Preferably, the cultivation vessel has a synthesis area of at most 50,000 cm$^2$, more preferably at most 20,000 cm$^2$, more preferably at most 1,000 cm$^2$, still more preferably at most 50 m$^2$, still more preferably at most 100 m$^2$. Particularly, the semi-static continuous process as described herein may allow for an advantageously high synthesis area, The cellulose of the inventive article is biotechnologically produced nano-structured cellulose, also referred to as "BNC" herein. In general, any cellulose-producing bacterial strain may be applied in the present invention. However, the BNC of the article of the present invention preferably is of the strain *Komatagaibacter xylinum*, also known as *Acetobacter xylinum*.

Preferably, the *K. xylinum* strain is selected from the group comprising ATCC 11142 and DSM 14666.

The BNC fleece produced by the method according to the present invention may advantageously be used directly as the article of the present invention or as the BNC content of the article according to the present invention.

Particularly, the cellulose-containing article comprises cellulose in an amount of at most 10%, preferably of at most 5% by weight.

The sum of fluid and cellulose, in the article, preferably is at least 80% by weight, in particular at least 90% by weight, in particular at least 95% by weight. In an embodiment the sum of the constituents fluid and cellulose in the article, preferably are essentially 100%. In other words, the article may essentially consist of a BNC fleece of fluid and cellulose, It is of particular advantage that the article as such can directly be used in skin application, particularly without the need for further supporting or fixing means.

The term "fluid" as used herein, preferably refers to water and/or a water-based fluid comprising water, particularly de-ionized water, in an amount of at least 80%, preferably at least 90%, more preferably at least 95%, still more preferably at least 99%, and still more preferably at least 99.9%, and still more preferably 100%.

A relatively low average thickness of the article allows for a convenient application by the subject. However, an article having an average thickness, which is too low, may more easily tear. The thickness of the article preferably is in average at least 0.5 mm, more preferably at least 0.8 mm, still more preferably at least 1.0 mm, still more preferably at least 1.5 mm, and still more preferably at least 2.0 mm. On the other hand, an article having an average thickness, which is too high, may cause an uncomfortable feeling and may not adhere to the skin without the need for further adherence or fixation means. The average thickness of the article preferably is at most 8.0 mm, more preferably at most 6.0 mm, still more preferably at most 5.0 mm. The average thickness of the article can be determined by usual methods known to the person skilled in the art, comprising e.g. vernier caliper measurements. The BNC characteristics allow for thin articles at good tensile strength.

Preferably, the article is a non-woven of fibers of the cellulose. This advantageously allows a relatively easy and cost-effective production. Particularly, the fibers of the cellulose have an average diameter of from 30 to 250 nm. The diameter is preferably determined from scanning electron microscopy (SEM) pictures.

The volumetric mass density of the article, particularly of the cellulose content of the article, is at least 0.50 g/cm$^3$, preferably at least 0.55 g/cm$^3$. The volumetric mass density of the article, particularly of the cellulose content of the article, is at most 1.50 g/cm$^3$, preferably at most 1.25 g/cm$^3$.

The volumetric mass density of the article, particularly of the cellulose content of the article, preferably is from at least 0.50 g/cm$^3$ to at most 1.50 g/cm$^3$, more preferably from at least 0.55 g/cm$^3$ to at most 1.50 g/cm3, still more preferably from at least 0.50 g/cm$^3$ to at most 1.25 g/cm$^3$, and most preferably from at least 0.55 g/cm$^3$ to at most 1.25 g/cm$^3$.

In order to achieve a density that is required to obtain optimum adhesion of the article to the skin the amount of bacteria and nutritional compositions in the culturing medium can be advantageously adjusted.

The weight-average molecular weight $M_w$ of the article, particularly of the cellulose of the article, preferably is at most 1,500,000 g/mol, more preferably at most 1,200,000 g/mol, more preferably at most 1,000,000 g/mol, more preferably at most 900,000 g/mol, at most 850,000 g/mol, at most 800,000 g/mol, most preferably at most 780,000 g/mol. If the weight-average molecular weight $M_w$ is very high, the stability of the material may be impaired. The weight-average molecular weight $M_w$ of the article, particularly of the cellulose of the article, preferably is at least 100,000 g/mol, preferably at least 250,000 g/mol, at least 300,000 g/mol, at least 400,000 g/mol, most preferably at least 500,000 g/mol. If the weight-average molecular weight $M_w$ is very low, the desired poly-dispersity index may not be achieved as described below.

The number-average molecular weight $M_n$ of the article, particularly of the cellulose of the article, preferably is at most 500,000 g/mol, preferably at most 400,000 g/mol, at most 450,000 g/mol, at most 400,000 g/mol, most preferably at most 360,000 g/mol. If the number-average molecular weight $M_n$ is very high, the desired polydispersity index may not be achieved as described below. The number-average molecular weight $M_n$ of the article, particularly of the cellulose of the article, preferably is at least 100,000 g/mol, preferably at least 150,000 g/mol, at least 200,000 g/mol, at least 250,000 g/mol, most preferably at least 300,000 g/mol. If the number-average molecular weight $M_n$ is very low, the stability of the material may be impaired.

The degree of polymerization is the average number of monomeric units in the BNC polymers of a specific BNC network. It can be expressed as the ratio of the number-average molecular weight of the respective BNC polymers to the molecular weight of the monomeric unit.

The polydispersity index (PDI) is a measure of the heterogeneity of the molecular mass distribution of the BNC polymers of a respective BNC network. It is calculated as the ratio of the weight-average molecular weight to the number-average molecular weight of the respective BNC polymers. Higher PDI values indicate a broader molecular weight distribution of the BNC polymers of a BNC network. The length of the cellulose chains of the article are preferably relatively uniform, which may be reflected by a relatively low polydispersity index ($M_w/M_n$).

The PDI ($M_w/M_n$) of the article preferably is low. It is known that at a relatively low PDI refers to a more stable material and pore structure. A PDI of nearly 1 would reflect a homogenicity which is nearly optimal. According to at least some embodiments, preferably the polydispersity index PDI ($M_w/M_n$) of the article is less than 3.5, preferably less than 3.0, more preferably less than 2.75 and still more preferably less than 2.5, still more preferably less than 2.0, still more preferably less than 1.75, and most preferably less than 1.5.

According to at least some embodiments, preferably the article is characterized by a DPn of at least 1,000, more preferably at least 1,500, more preferably at least 1,700. Preferably, the article is characterized by a DPn of at most 5,000, more preferably at most 3,000, still more preferably at most 2,500, still more preferably at most 2,200.

Preferably the article according to the present invention comprises glycerin in an amount of at most 30% by weight, more preferably of at most 15% by weight, still more preferably at most 10% by weight, most preferably of at most 5% by weight. In one particular embodiment, the article according to the present invention comprises no glycerin. Glycerin may disadvantageously result in unwanted material properties, particularly a higher weight of the article.

The cellulose content of the article preferably comprises carbonyl groups in an amount of less than 8.5 µmol/g, preferably of less than 8.0 µmol/g, more preferably of less than 7.5 µmol/g, still more preferably of less than 7.0 µmol/g, still more preferably of less than 6.0 µmol/g, and still more preferably of less than 5.75 µmol/g. The cellulose con-tent of the article preferably comprises carbonyl groups in an amount of at least 1.0 µmol/g, more preferably of at least 1.5 µmol/g, still more preferably of at least 2.0 µmol/g, still more preferably of at least 2.5 µmol/g, and most preferably of at least 2.75 µmol/g.

For cellulose, particularly, cellulose-containing articles, the crystallinity Ic is an important parameter. The degree of crystallinity is preferably determined by NMR spectroscopy. A low crystallinity Ic may particularly be accompanied by a decrease in the permeability for gases and liquids. For the purpose of the present invention, particularly the inventive article and its use in the inventive method of treatment, a relatively high crystallinity Ic is desired, in order to provide a relatively high permeability for gases and liquids. The crystallinity Ic of the cellulose of the article is at least at least 55%, more preferably at least 60%, more preferably at least 65%, more preferably at least 70, most preferably at least 80%. Preferably, all crystallinity Ic of the cellulose of the article is at most 95%, more preferably at most 90%, more preferably at most 85%.

A person skilled in the art will recognize that BNC exists in several crystalline polymorphs. Moreover, BNC simultaneously crystallizes in a one-chain triclinic structure Iα, and a two-chain modification Iβ. Both polymorphs are packed in a parallel chain arrangement, but of various ratios in a cellulose-containing article, depending on the origin and method of manufacturing. Preferably, the cellulose of the inventive article comprises cellulose Iα in an amount of at least 10%, preferably at least 20%, more preferably at least 30% by weight of the article. Preferably, the cellulose of the inventive article comprises cellulose Iα in an amount of at most 90%, preferably at most 70%, more preferably at most 50% by weight of the article. Additionally or alternatively, the cellulose of the inventive article comprises cellulose Iβ in an amount of at least 1%, preferably at least 5%, more preferably at least 10% by weight. Preferably, the cellulose of the inventive article comprises cellulose Iβ in an amount of at most 90%, preferably at most 80%, more preferably at most 70%, still more preferably at most 60%, still more preferably at most 50%, and most preferably at most 45% by weight. Preferably, the amount of cellulose Iα and Iβ is determined on the basis of CP/MAS 13C NMR. The above ranges are preferable to achieve the desired properties of the article.

Particularly, the inventive article may comprise cellulose Iα and cellulose Iβ in a mass ratio of at most 2.75, preferably at most 2.5, more preferably at most 2.4. Preferably, the inventive article comprises cellulose Iα and cellulose Iβ in a mass ratio of at least 1.5, preferably at least 2.0, more preferably at least 2.25. The above ratios are preferable to achieve the desired properties of the article.

For the purpose of the present invention the article provides fluid, particularly water, and optionally at least one active agent, to the treated area of skin. A preferable water absorption capacity (WAC) and/or a preferable water retention capacity of the article may allow for an increase in the desired effect of treatment. Particularly, the inventive article may have a water absorption capacity (WAC) of at least 80%, more preferably at least 120%, more preferably at least 150%. As described herein, the water absorption capacity is calculated by the following formula $$WAC = mass(wet)/mass(dry)*100\%.$$

Preferably, the article has a water absorption capacity (WAC) of at most 300%, more preferably at most 250%, and still more preferably at most 200%. Optionally and preferably, the article has a water absorption capacity (WAC) of from 150% to 200%. The water retention capacity (WRC) of the inventive article may be of at least 500%, preferably at least 600%, more preferably at least 700%, most preferably at least 750%. The water retention capacity (WRC) of the inventive article may be of at most 1,500%, preferably at most 1,250%, more preferably at most 1,000%, most preferably at most 950%. The water retention capacity (WRC) as used herein is the ratio of wet mass at maximum WAC and dry mass determined after centrifugation of the article for 15 min at 5,000 rpm.

Preferably, the article has a moist vapor transmission rate in the wet state of at least 100 g/($m^2$*24h), more preferably at least 200 g/($m^2$*24h), more preferably at least 500 g/($m^2$*24h). Preferably, the multi-phase biomaterials have a moist vapor transmission rate in the wet state of at most 3,000 g/($m^2$*24h), more preferably at most 2,000 g/(m2*24h), more preferably at most 1,000 g/($m^2$*24h). Particularly preferably, the multi-phase biomaterials have a moist vapor transmission rate in the wet state of from 500 g/($m^2$*24h) to 1,000 g/($m^2$*24h). Preferably, the moist vapor transmission rate is determined according to DIN EN 13726-2:2002.

In order to provide an article which advantageously adapts to the skin area to be treated, particularly to the geometry and dimensions of the face, the tensile strength of the article is of importance. Particularly, a too low tensile strength will not allow that the article is stretchable and thus will not allow that the article adapts to the unevenness of the skin, particularly the unevenness of the face. The tensile strength of the inventive article preferably is more than 100

MPa, preferably more than 252 MPa, preferably more than 275 MPa, more preferable more than 300 MPa, and most preferably of more than 310 MPa. The tensile strength of the inventive article preferably is less than 1,000 MPa, preferably less than 750 MPa, more preferably less than 500 MPa, and most preferably of less than 400 MPa. The tensile strength as referred to herein preferably is determined after hot pressing of the article using a TIRAtest 2710 universal measuring device with a nominal force of 1.5 kN. Preferably, the tensile strength as referred to herein is determined according to DIN EN ISO 527-1:2012-06 and/or DIN EN ISO 527-2:2012-06.

BRIEF DESCRIPTION OF THE DRAWINGS

The present invention will be described in further detail with reference to the drawings from which further features, embodiments and advantages may be taken, and in which:

FIGS. 1A to 1G illustrate cutting patterns of cellulose-containing articles according to the present invention. Particularly, FIGS. 1A and 1B show the cutting pattern of an inventive cellulose-containing articles adapted to be applied on the face (face mask)

Figure 1A:
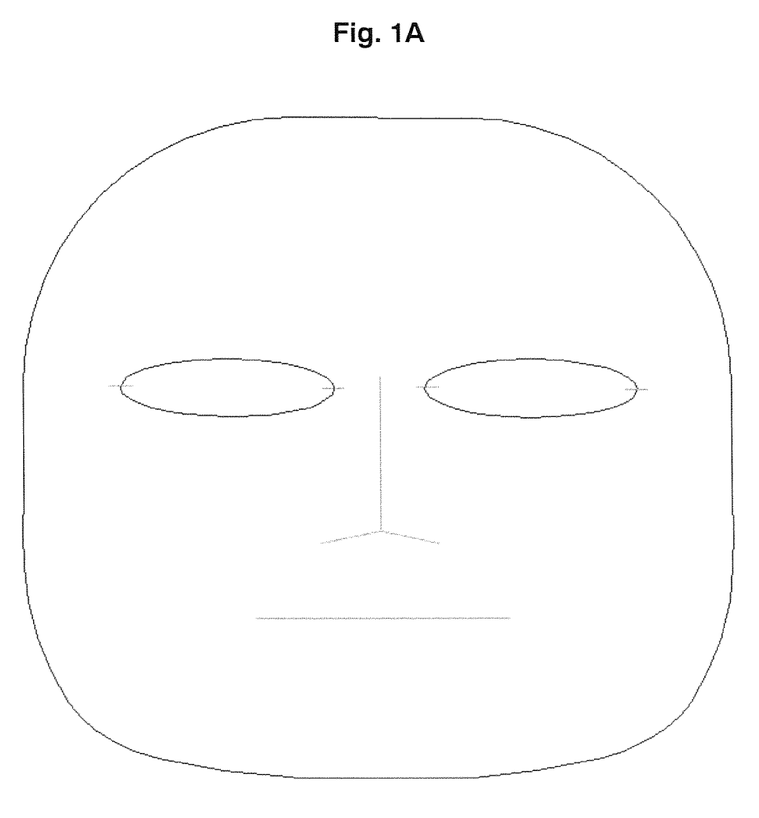
Figure 1B:
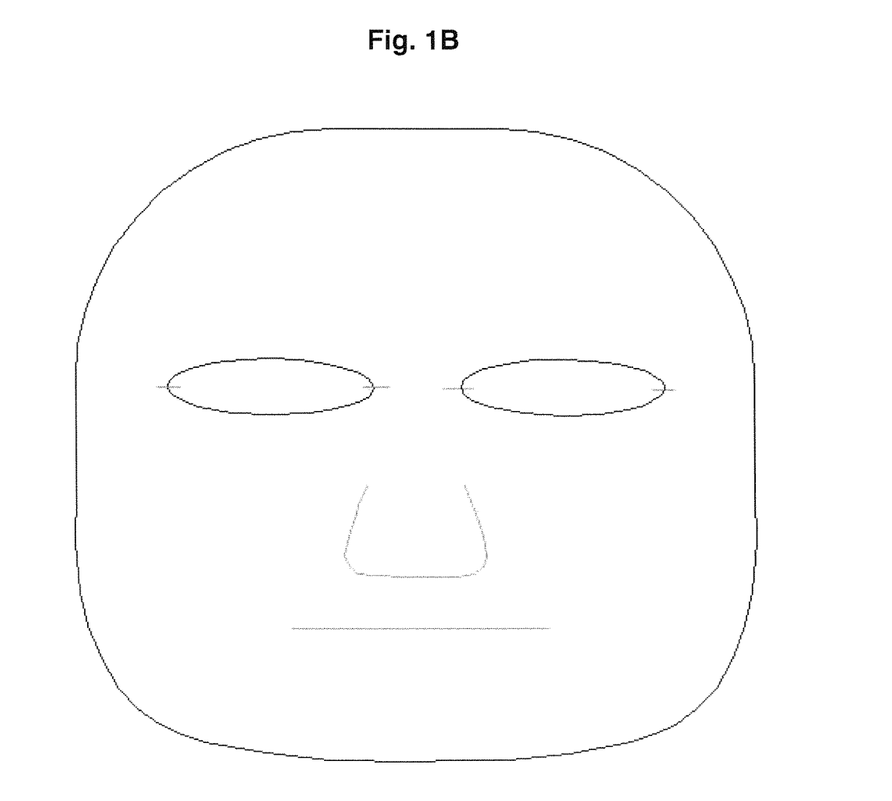

The face mask as shown in FIGS. 1A and 1B may particularly be provided with an average thickness of about 2 mm or with an average thickness of about 0.8 to 1 mm. The face mask may have a width of 185 mm and a height of 175 mm. Alternatively, the face mask may be provided with a width of 240 mm and a height of 175 mm.

Figure 1C:
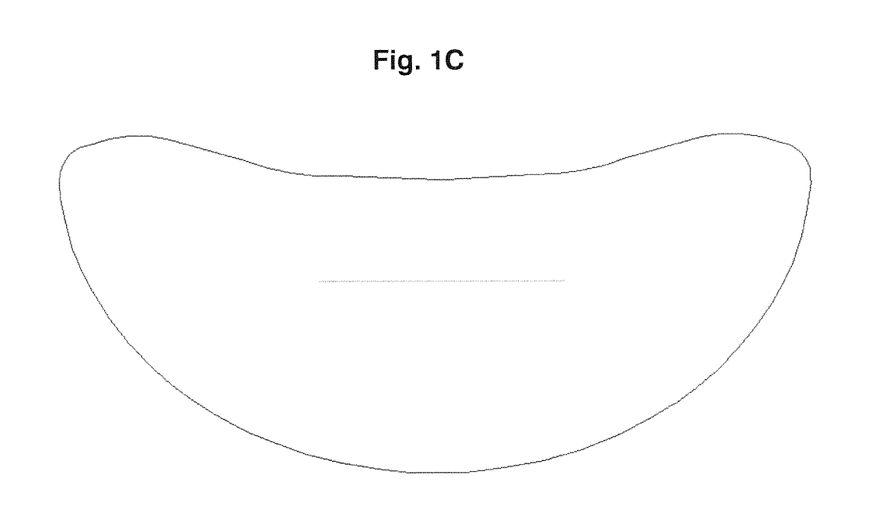
FIG. 1C shows the cutting pattern of an inventive cellulose-containing article adapted to be applied on or around the mouth (mouth mask)

The mouth mask as shown in FIG. 1C may particularly be provided with an average thickness of about 1 mm. Alternatively the mouth mask may be provided with an average thickness of about 2 mm. The mouth mask may have a width of 125 mm and a height of 85 mm.

Figure 1D:
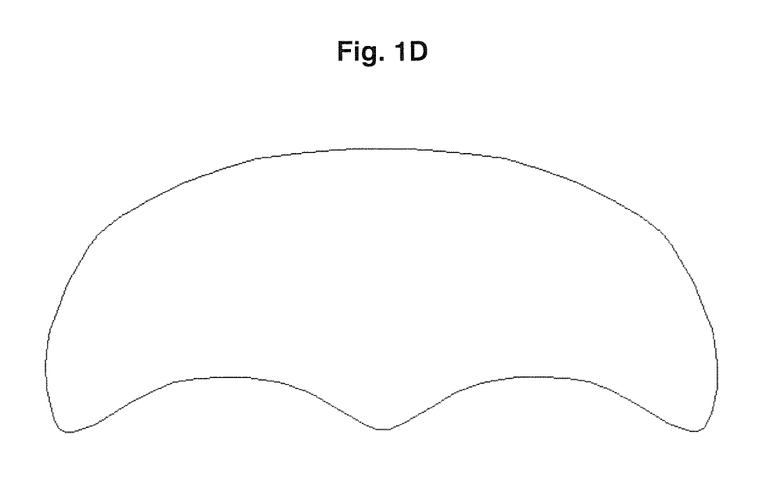
FIG. 1D shows the cutting pattern of an inventive cellulose-containing article adapted to be applied on the forehead (forehead mask)

The forehead mask as shown in FIG. 1D may particularly be provided with an average thickness of about 1 mm. Alternatively the forehead mask may be provided with an average thickness of about 2 mm. The forehead mask may have a width of 190 mm and a height of 60 mm.

Figure 1E:
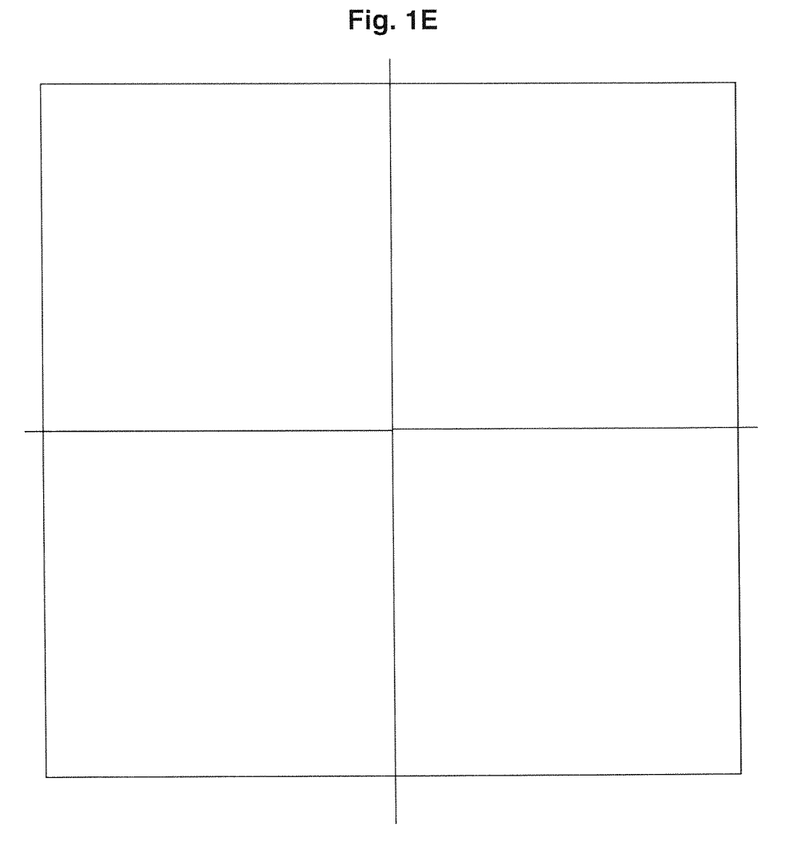
FIG. 1E shows the cutting pattern of an inventive cellulose-containing article in the form of a 10 cm×10 cm overlay.

The overlay as shown in FIG. 1E may particularly be provided with an average thickness of about 2 mm. Alternatively, the overlay may be provided with an average thickness of about 0.8 to 1 mm. The overlay may have a width of 100 mm and a height of 100 mm.

Figure 1F:
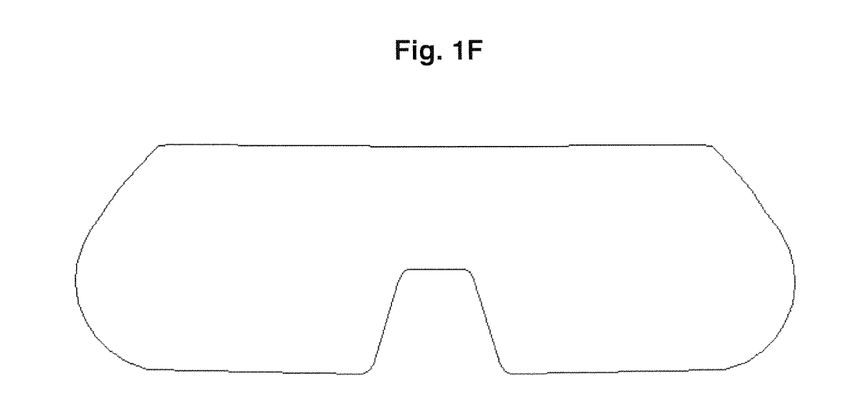
FIG. 1F shows the cutting pattern of an inventive cellulose-containing article adapted to be applied on the eyes (eye mask)

The eye mask as shown in FIG. 1F may particularly be provided with an average thickness of about 2 mm. Alternatively the eye mask may be provided with an average thickness of about 1 mm. The eye mask may have a width of 191 mm and a height of 60 mm.

Figure 1G:
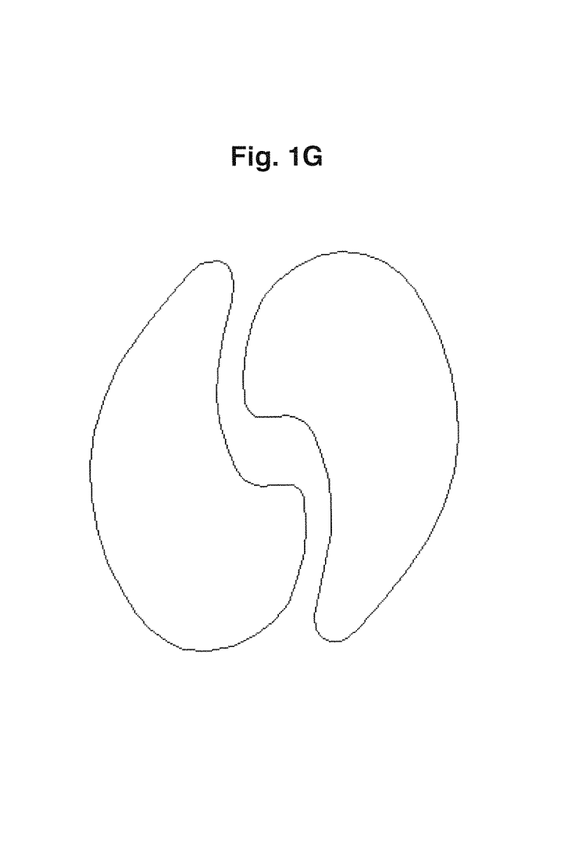
FIG. 1G shows the cutting pattern of an inventive cellulose-containing article adapted to be applied on single eyes (eye pads).

The eye pads as shown in FIG. 1G may particularly be provided with an average thickness of about 1.0 to 2.0 mm. The eye pads may have each a width of 75 mm and a height of 35 mm.

DETAILED DESCRIPTION OF THE INVENTION

Example 1

The cellulose-containing article according to the present invention and manufactured using a semi-static continuous process was compared with regard to its material characteristics to a cellulose-containing article manufactured using a static and discontinuous culture (comparative example).

Molecular Structure

The molecular structure of the article according to the present invention was determined using gel permeation chromatography (GPC).

For this purpose cellulose of the strain ATCC 11142 was used. The comparative example was produced using a static cellulose manufacturing process. The article according to the present invention was produced using a continuous semi-static cellulose manufacturing process.

The GPC-measurement was performed using 0.9% (m/v) LiCl/DMAc-solution according to Röder et al (RÖDER T, MORGENSTERN B, SCHELOSKY N, GATTER O: Solutions of cellulose in N,N-dimethylacetamide/LiCl by light scattering methods. Polymer (2001), 42/16, 6765-73.) with dissolved dry-frozen BC samples and was performed using four serial GPC-columns (PL Gel ALS, 20 μm, 7.5×300 mm) and using three detectors (Fluorescence, MALLS and Refraction index). An 0.9% (m/v) LiCl/DMAc-solution was used as the eluent. Filtration was performed using an 0.02 μm-filter. The flow rate was 1 ml/min, the injection volume was 100 μl and the running time was 45 min. For labeling of the carbonyl groups a fluorescence marker was used and measured fluorometrically. For evaluation the program CS53_76-79 according to Röhrling et al. (RÖHRLING J, POI I HAST A, ROSENAU T, LANGE T, EBNER G, SIXTA H, KOS-MA P A: Novel method for the determination of carbonyl groups in cellulosics by fluorescence labelling. 1. Method development. Biomacromolecules (2002), 3, 959-68) was used.

Table 1 shows the results. Particularly, the molecular characteristics are shown in table 1 of an article according to batches of articles according to the present invention (sample 1 and sample 2), and one comparative example.

TABLE 1

| | $M_n$ [g/mol] | $DP_n$ [$M_n/M_0$] | $M_w$ [g/mol] | PDI [$M_w/M_n$] | Carbonyl-groups [μmol/g] | Carbonyl-endgroups [μmol/g] |
|---|---|---|---|---|---|---|
| comparative example | 308300 | 1902 | 1069000 | 3.5 | 8.50 | 3.24 |
| sample 1 | 305200 | 1882 | 775800 | 2.5 | 5.61 | 3.28 |
| sample 2 | 355900 | 2195 | 627100 | 1.8 | 3.46 | 2.80 |

Thereby, the amount of carbonyl-end-groups was determined based on DPn.

The present inventors have surprisingly found that the length of the cellulose chains of samples 1 and 2, manufactured using a continuous semi-static process are more uniform than the cellulose chains of the comparative example, manufactured with a static culturing. This is particularly reflected by the relatively low PDI-value of sample 1 and sample 2. The comparative example, however, comprises a mixture of long- and short chains of cellulose. This also explains the differences shown between the theoretical and the experimentally determined value of the amounts of carbonyl groups Near Structure The near structure of the article according to the present invention was determined using NMR.

For this purpose cellulose of the strain ATCC 11142 and of the strain DSM 14666 was used. The comparative example was produced as a wet fleece using a static cellulose manufacturing process. The article according to the present invention was produced as a wet fleece using a continuous semi-static cellulose manufacturing process.

For determination of cellulose $I\alpha$ and $I\beta$ as well as the crystallinity of never-dried BC-samples solid-state-13C-NMR-spectroscopy was performed. The 13C-CP-MAS having a TPPM decoupling (4 mm High-Kopf) was performed using a 400 MHz-Avance II-Spectrometer of Bruker, at a static magnetic field of 9,4 T. The rotational frequency in the measurement of the sample was 5 kHz and the relaxation time (the time between the scans) was 2 seconds.

Figure 2:
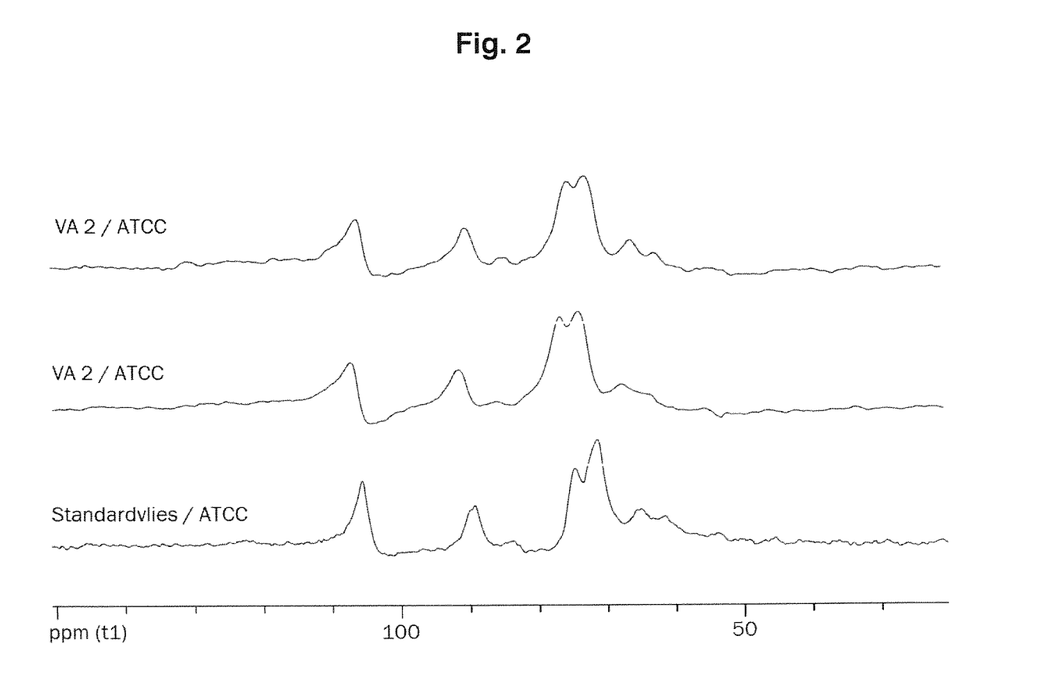
FIG. 2 shows the CP/MAS 13C-spectra of cellulose of the strain ATCC 11142 (upper panel) and of the strain DSM 14666 (middle panel) manufactured using a continuous semi-static cellulose manufacturing process in comparison to the comparative example (lower panel).

FIG. 2 shows the CP/MAS 13C-spectra of cellulose of the strain ATCC 11142 (upper panel) and of the strain DSM 14666 (middle panel) manufactured using a continuous semi-static cellulose manufacturing process in comparison to the comparative example (lower panel). It is immediately apparent therefrom that also in the CP/MAS 13C-spectra the samples from the continuous semi-static manufacturing method differ in the samples from the static manufacturing method. Table 2 below shows the content of cellulose $I\alpha$ and $I\beta$, respectively, and the crystallinity Ic based on the CP/MAS 13C NMR.

The results of the NMR experiment confirm the results achieved by the above-described GPC-analysis.

TABLE 2

| strain | | $I\alpha$ [%] | $I\beta$ [%] | $I\alpha/I\beta$ | Ic [%] |
|---|---|---|---|---|---|
| DSM 14666 | comp. example | 43 | 20 | 2, 2 | 86 |
| | inventive sample | 40 | 17 | 2, 4 | 86 |
| ATCC 11142 | comp. example | 35 | 15 | 2, 2 | 81 |
| | inventive sample | 34 | 14 | 2, 4 | 82 |

Supra Molecular Structure

The supra molecular structure was determined using REM in 2,000-fold magnification after labeling with leading carbon and subsequent gold sputtering. Electron-microscope Leica S440i, with tungsten cathode to maximum of 30 kV, scintillation-SE-detector, 4-quadrantfield semi-conductor RE-detector. The respective BNC fleeces of cellulose of the strain ATCC 11142 and of the strain DSM 14666 were freeze-dried and subsequently subjected to REM. It was found that independent of the utilized strain the supra molecular structure of the inventive samples (continuous semi-static cellulose manufacturing process) was indistinguishable from the supra molecular structure of the comparative samples (static cellulose manufacturing process).

Surface Structure

The surface structure of cellulose-containing articles is of importance, particularly if applied as wound dressing or cosmetic product. The surface structure was analyzed using laser scanning microscopy-(LSM). For this purpose BNC-fleeces of strains ATCC 11142 and DSM 14666, respectively, were produced in a static process and in a semi-static continuous process, respectively.

Hot pressing of the samples was performed at 120° C. for 10 min (d≤50 µm) or 20 min (d≥50 µm) using Yellow Press 4050/Schulze Thermal Transfer Press.

LSM-pictures of the upper surfaces and the lower surfaces of wet fleeces of the bacterial strain ATCC 11142 produced in a semi-static continuous process and in a static process revealed that the surface structure of fleeces produced in a semi-static continuous process was indistinguishable of the surface structure of fleeces produced in a static process.

Water Absorption Capacity, Water Retention Capacity and Tensile Strength

BNC by nature forms a hydro gel, which results in its characteristic liquid affinity of water or other organic solutions. Thereby, the water absorption capacity and the water retention capacity of the BNC-articles are important features.

After purification of the BNC-samples and consecutive washing steps using a.dest until the washing water was neutral (determined with unitestpaper), the average weight of the never-dried samples was determined.

The WRC was determined using standardized conditions as described in Jayme & Rothamel (JAYME G, ROTHAMEL L: Composition of the extractives obtained from black poplarwood and of those found in the resulting sulfite and sulfate pulps. Cellulose-Chemie (1944), 22, 88-96). The samples to be determined were cut into pieces of 0.5 cm2. The never-dried BNC-samples were centrifuged for 15 min, at 4000 U/min (rpm) and the wet weight was determined. 4000 rpm correspond to about 1788 g. After air drying at 100° C. in a drying chamber to constant weight, the WRC was determined using the quotation $$WRC=(\text{mass wet}-\text{mass dry})/\text{mass wet}\times 100\%$$

The re-quelling of the dried samples was performed at 30° C. for 2 hrs. in a.dest.

Table 3 shows the water absorption capacity (WAC) and the water retention capacity (WRC) of wet BNC fleeces of the respective bacterial strain manufactured in a semi-static continuous process and in a static process, respectively.

TABLE 3

| Strain | manufacturing method | WAC [%] | WRC [%] |
|---|---|---|---|
| DSM 14666 | static | 16 900 ± 1.520 | 853 ± 94 |
| DSM 14666 | semi-static, continuous | 14.000 ± 1.260 | 900 ± 99 |
| ATCC 11142 | static | 13.195 ± 1.310 | 815 ± 85 |
| ATCC 11142 | semi-static, continuous | 11.003 ± 1.083 | 781 ± 83 |

Furthermore the tensile strength was determined. The tensile strength is a preferable measure for the uniformity of the BNC. The BNC fleeces were hot pressed. The BNC fleeces manufactured in a semi-static continuous process revealed a higher tensile strength compared with the BNC fleeces manufactured in a static process. BNC fleeces manufactured in a static process showed a tensile strength of 252 MPa, whereas BNC fleeces manufactured in a semi-static continuous process showed a bending tensile strength of 312 MPa.

The features of the present invention disclosed in the specification, the claims, examples and/or the figures may both separately and in any combination thereof be material for realizing the invention in various forms thereof.

What is claimed is:

1. A method of manufacturing an article containing biotechnologically produced nanostructured cellulose (BNC), comprising:

providing a BNC non-woven in a continuous semi-static process, including producing BNC from a bacterial culture in a cultivation medium, and providing the article, the article comprising BNC of microbial origin in an amount of at least 1% by weight and at most 15% by weight; and fluid in an amount of at least 85% by weight and at most 99% by weight; and wherein the article comprises carbonyl groups in an amount of less than 8.0 µmol/g.

2. The method according to claim 1, wherein the fluid comprises water.

3. The method according to claim 1, comprising the step of:

adding cultivation medium and/or constituents of the cultivation medium during bacterial culture.

4. The method according to claim 1, comprising the step of:

harvesting or removing BNC non-woven from the bacterial culture during BNC synthesis.

5. The method according to claim 4, wherein harvesting or removing BNC non-woven is done stepwise or continuously.

6. The method according to claim 1, wherein providing the BNC non-woven comprises, providing a reaction vessel comprising cultivation medium;

inoculating the cultivation medium with a BNC-producing bacterial strain; and bacterial synthesis of BNC in the reaction vessel.

7. The method according to claim 1, wherein a cell count is from $10^4$ to $10^7$ cells/ml of cultivation medium during the culture.

8. The method according to claim 1, wherein the cultivation medium comprises a carbon source, a nitrogen source and/or a vitamin source.

9. The method according to claim 1, wherein the cultivation medium comprises a buffer.

10. The method according to claim 8, wherein the cultivation medium comprises the carbon source in an amount of at least 10 g/l.

11. The method according to claim 8, wherein the cultivation medium comprises the nitrogen source in an amount of at least 2 g/l.

12. The method according to claim 8, wherein the cultivation medium comprises the vitamin source in an amount of at least 2 g/l.

13. The method according to claim 1, wherein a cultivation temperature is at least 20° C. and/or at most 36° C.

14. The method according to claim 1, wherein a cultivation time is at least 1 day.

15. The method according to claim 1, wherein a culture volume is at least 10,000 ml.

16. The method according to claim 1, wherein a synthesis area is at least 10 m$^2$.

17. The method according to claim 1, wherein a weight average molecular weight of the BNC is at most 1,000,000 g/mol.

18. The method according to claim 1, wherein providing the article includes adapting the article's shape to an area of skin, including the face, a part of the face, the mouth, forehead, or the eyes.

19. The method according to claim 1, wherein providing the article includes cutting the non-woven to the desired shape.

20. The method according to claim 19, wherein cutting is performed with a fluid jet.

21. The method according to claim 20, wherein the fluid jet has a diameter of from 100 to 300 µm.

22. The method according to claim 1, comprising sterilizing the article.

23. The method according to claim 22, wherein sterilizing is e-beam sterilization.

* * * * *